United States Patent [19]

Wright

[11] Patent Number: 4,659,663

[45] Date of Patent: Apr. 21, 1987

[54] METHODS FOR ISOLATING CELL FUSION PRODUCTS

[75] Inventor: Woodring E. Wright, Irving, Tex.

[73] Assignee: Board of Regents, University of Texas System, Austin, Tex.

[21] Appl. No.: 656,658

[22] Filed: Oct. 1, 1984

[51] Int. Cl.⁴ .................. C12P 21/00; C12N 15/00; C12N 5/00; C12R 1/91

[52] U.S. Cl. .................. 435/172.2; 435/68; 435/240; 435/948; 935/90

[58] Field of Search .............. 435/68, 172.2, 240, 435/948; 935/90, 93, 92

[56] References Cited

PUBLICATIONS

Wright, W. E. Proc. Natl. Acad. Sci. USA 81: 7822–7826, Dec. 1984.

Wright, W. E. (1984), "Induction of Muscle Genes in Neural Cells," J. Cell Biol., 98:427–435.

Spitz, M., Spitz, L., Thorpe, R. and Eugui, E. (1984), "Intrasplenic Primary Immunication for the Production of Monoclonal Antibodies," J. Immunol. Meth., 70:39–43.

Wright, W. E. (1982), "The Selection of Heterokaryons and Cell Hybrids Using the Biochemical Inhibitors Iodoacetamide and Diethylpyrocarbonate," in Techniques in Somatic Cell Genetics, edited by Jerry W. Shay, Plenum Publishing Corporation.

Okada, C. Y. and Rechsteiner, J. (1982), "Introduction of Macromolecules into Cultured Mammalian Cells by Osmotic Lysis of Pinocytic Vesicles," Cell, 29:33–41.

Hohmann, L. K. and Shows, T. B. (1979), "Complementation of Genetic Disease: A Velocity Sedimentation Procedure for the Enrichment of Heterokaryons," Som. Cell Genetics, 5:1013–1029.

Jongkind, J. F., Verkerk, A. and Tanke, H. (1979), "Isolation of Human Fibroblast Heterkaryons with Two-Colour Flow Sorting (FACS II)," Exp. Cell Res., 120:444–448.

Eisenberg, L. R. and Migeon, B. R. (1979), "Enrichment of Human Heterokaryons by Ficoll Gradient for Complementation Analysis of Iduronate Sulfatase Deficiency," Som. Cell Gen., 5:1079–1089.

Olsnes, S. and Pihl, A. (1973), "Isolation and Properties of Abrin: A Toxic Protein Inhibiting Protein Synthesis," Eur. J. Biochem., 35:179–185.

Julius, M. H., Masuda, T. and Herzenberg, L. A. (1972), "Demonstration that Antigen-Binding Cells are Precursors of Antibody-Producing Cells after Purification with a Fluorescence-Activated Cell Sorter," Proc. Nat. Acad. Sci. USA, 5, 69:1934–1938.

Littlefield, J. W. (1964), "Selection of Hybrids from Matings of Fibroblasts In Vitro and their Presumed Recombinants," Science, 145:709–710.

Primary Examiner—Thomas G. Wiseman
Assistant Examiner—Karen Maurey
Attorney, Agent, or Firm—Arnold, White & Durkee

[57] ABSTRACT

A method for isolating the fusion product of two cell populations is disclosed. The method involves the introduction of a specific antitoxin into cells of one population while introducing a second specific antitoxin into cells of the second population. After fusing cells of the first population with those of the second population, the fusion product may be selectively isolated on a medium containing an appropriate amount of both first and second toxins. For some applications, it may be appropriate to introduce an antitoxin into only one of the cell populations and isolate the fusion product on a media containing only one toxin.

20 Claims, No Drawings

METHODS FOR ISOLATING CELL FUSION PRODUCTS

BACKGROUND OF THE INVENTION

THe Goverment may have rights in this invention pursuant to National Institutes of Health Grant No. AGO1228.

The present invention relates to procedures for isolating fused cells which are formed by the fusion of two or more individual mononucleate cells into a single multinucleate cell, the heterokaryon. More particularly, this invention relates to a toxin-antitoxin selection technique whereby fused cells may be selected from a mixture which contains unfused parental cells.

The technique of inducing the fusion of human, animal, and plant cells of different origins to produce cell hybrids has become a widely used one, with important applications to somatic cell genetics and to fields of practical concern such as medicine and agriculture. Somatic cell hybridization has proved to be an extremely powerful experimental procedure for genetic manipulation in cell biology, genetics, developmental biology, tumor biology, and virology.

Basically the technique involves the spontaneous or induced fusion of different cells to give a cell hybrid. A wide variety of animal, human, and even insect and plant cell types have been used as parental cells in these fusions. When cells of different organisms are fused (e.g., mouse and man, hen and rat, mosquito and man), interspecific hybrid cells are produced. In these cases, the parental cells differ at least with respect to genotype if not phenotype as well. Intraspecific hybrids are obtained by fusing two different cell types from the same species or organism (e.g., mouse fibroblasts and mouse lymphoblasts; epidermal cells and lung cells; liver cells and bone cells). Intraspecific hybrids may also be formed by the fusion of the same cell type from different individuals of the same species (e.g., fibroblasts from an older individual with those of a younger individual). In these instances the parental cells differ in phenotype, that is, in morphological, biochemical, immunological, or functional properties.

Spontaneous fusion of cells occurs infrequently under laboratory culture conditions and also occasionally in living organisms. The present standard laboratory procedure for induciing cell hybrids in vitro involves addition of polyethylene glycol (PEG) to a cell culture containing two different cell types. Using this procedure, two groups of multinucleate cells (polykaryons) are generated. The first group contains nuclei from only one parental type (homokaryons), while the second group contains nuclei from both parental types (heterokaryons).

A heterokaryon which has been formed by one of various procedures has the potential to undergo a mitotic division, usually giving rise to two mononucleate daughter hybrid cells called synkaryons. In the current literature, these synkaryons are generally referred to as hybrid cells. Therefore, the initial multinucleate, fused cells are referred to as heterokaryons whereas the mononucleate progeny are hybrid cells. It should be remembered, though, that heterokaryons are in fact also hybrid cells.

As noted above, a single cell fusion experiment may contain unfused parental cells and numerous cell fusion products including heterokaryons, synkaryons, and other hybrid cells. For certain applications, the investigator may wish to look at only the heterokaryons. For other applications, it may be necessary to prepare large numbers of hybrid cells. In a few instances, cell fusions may give rise to predominantly pure populations of hybrid cells because the hybrid cells proliferate more rapidly than either of the parental cell types and therefore overgrow them. In most instances, however, the hybrid cell populations grow more slowly and tend instead to be overgrown by the parental cells. Therefore, one of the major problems facing scientists who desire to work with cell fusion products is how to selectively isolate hetefokaryons or hybrid cells away from the parental cells.

In general, populations enriched for cell fusion products are presently isolated by one of two general approaches: selectively or nonselectively. Nonselective isolation involves mechanically separating hybrid cells from the remainder of the cells in culture. Mechanical separation has been accomplished both manually and by gradient or velocity sedimentation. Cells that have been mechanically isolated by one of these techniques can be allowed to proliferate into colonies of cells. A major difficulty presented by these techniques is that hybrid cells generally represent such a small minority of the cells present, that they are not easily isolated. Photoactivated cell sorters have been utilized to increase the accuracy of fused cell isolation. This technology is extremely expensive, and relies on the availability of appropriate photoactive molecules (to identify each cell type) that can be excited by the cell sorter. Even if the hybrid cells are successfully isolated, their numbers may be so few that they will fail to proliferate for various reasons. This in turn may require the isolation of vast numbers of hybrid cells, which can be a very expensive and time consuming proposition.

On the other hand, selective isolation techniques presently employed involve the culturing of mixed cell cultures on a special medium which allows only hybrid cells to multiply. Both parental cell types are overgrown or die. When only synkaryons remain, single cells may be cloned in order to ensure that the resultant population consists of only one type of hybrid cell.

By far the most prevalent technique for selective isolation of cell hybrids in use today is the so-called HAT-selection. In the early 1960's it was demonstrated that it is possible to obtain mutant cells defective in specific enzymes by subjecting a normal cell population to selection with drugs. Utilizing this finding, a method for the isolation of hybrid cells was developed. In general, the technique utilizes two mutant cell types in the initial cell fusion: one cell type to be used in the subsequent fusion is resistant to azaguanine, a metabolic inhibitor; while the second cell type is resistant to another metabolic inhibitor, bromodeoxyuridine. Azaguanine, and the related drug thioguanine, are metablic inhibitors that are activated by the enzyme hypoxanthineguanine phosphoribosyl transferase (HGPRT). Therefore, cells which are resistant to azaguanine and thioguanine are generally lacking the HGPRT enzyme.

Bromodeoxyuridine-resistant cells are obtained by a similar procedure. In normal cells, this drug will first be phosphorylated by the enzyme, thymidine kinase (TK) and then incorporated into the cellular DNA. Similar to the HGPRT-mediated activation of azaguanine, thymidine kinase activates bromodeoxyuridine. Therefore, bromodeoxyuridine-resistant cells are generally lacking the enzyme thymidine kinase.

Since these enzymes are only involved in salvage pathways for nucleotide synthesis, the genetic defects are of little importance during growth on normal tissue culture media. But when the main bio-synthetic pathways for purine and pyrimidine nucleotides are blocked by the folic acid analogue aminopterin, normal cells can survive if supplied with exogenous hypoxanthine and thymidine whereas the mutant cells die because of their inability to synthesize nucleotides from hypoxanthine ($HGPRT^-$ cells) or from thymidine ($TK^-$ cells).

In the drug resistance hybrid cell selection system, hybrid cells are isolated after fusion of azaguanine resistant cells (which lack HGPRT but which have TK) with cells that are resistant to bromodeoxyuridine (which lack TK but which have HGPRT). Since the cell fusion products contain the thymidine kinase from one parent and the HGPRT enzyme from the other, the cell hybrids have both enzymes and are thus able to grow in a medium containing Hypoxanthine, Aminopterin, and Thymidine, the so-called HAT medium. Under the selective conditions presented by the HAT medium, *only* those cells carrying the genetic complement of *both* parental cell types could survive.

The HAT selection technique is not the only technique utilizing metabolic inhibitors. Other similar approaches are known, however, they all have similar drawbacks. The main limitation of these selection techniques is the requirement that both parental cell types have a *defined* genetic deficiency. Thus the selection technique is not generally applicable to all cell fusion experiments.

A second problem is the general inability to isolate heterokaryons as opposed to cell hybrids. As pointed out above, most selective systems for isolating fusion products between different cell types rely on the preferential ability of the fusion products to grow in a special medium. Because these selection systems require cell division, most experiments in somatic cell genetics have studied clones of cell hybrids rather than heterokaryons, which are the immediate product of the fusion of two different cells. However, there are many fundamental differences between hybrids and heterokaryons that make the latter an important subject of investigation. One of the most significant differences is that most differentiated cells are slowly dividing or post-mitotic. Restricting the analysis to only those fusion products capable of rapid cell division and clone formation thus automatically biases results against the expression of differentiated functions. This bias is particularly compelling if one examines the frequency with which heterokaryons give rise to growing hybrid clones. Although this varies widely with the cell combination employed and ranges from as much as one in three to as few as one in 100,000, an average value appears to be that about one in 100 heterokaryons gives rise to a hybrid clone. These clones thus represent a highly selected subset of all fusion products. In addition, heterokaryons provide a system in which different kinds of experimental information may be obtained than in the case of cell hybrids.

In light of these and other drawbacks in the prior art technology for the isolation of cell fusion products, there is a need for an isolation technique that is generally applicable to numerous cell types, that is reproducible, and relatively inexpensive.

SUMMARY OF THE INVENTION

In its broadest scope, the present invention provides a method for isolating cell fusion products which are produced by fusing one cell type with a second cell type. More particularly, the present invention provides for the isolation of heterokaryons, the initial binucleate or multinucleate fusion product of one cell type with a second cell type.

In accordance with the present invention, an antitoxin directed against a first toxin is introduced into the first cell type and an antitoxin directed against a second toxin is introduced into the second cell type. The two antitoxin-containing cell types are then mixed together under the appropriate conditions to promote fusion of the first cell type to the second cell type. After fusing the two cell types, the multinucleate fusion product, or heterokaryon, is isolated by culturing the fusion mixture in the presence of an appropriate amount of both toxins. Parental cells and fusion products of only one cell type contain only antibodies to a single toxin and therefore do not survive exposure to both toxins. However, heterokaryons may contain antibodies against both toxins and therefore are protected from the lethal effects of both toxins and are able to survive.

In one embodiment of the present invention, the first and second toxins are ricin and diphtheria toxin, respectively. Therefore, antibodies which are specific for ricin and diphtheria toxin, respectively, may be introduced separately into the two cell types to be subsequently fused. The heterokaryon fusion product can then be selected for at the culturing stage by including an appropriate amount of both ricin and diphtheria toxin in the growth medium. The heterokaryon, which will therefore contain antibodies to both toxins, will survive while other possible fusion products and parental cell will not.

In certain situations, there is no requirement for two separate toxins and antitoxins in isolating the fusion product of two cell populations. This occurs, for example, when one cell population, for whatever reason (e.g., an inability to grow in culture), need not be considered as a possible contaminating factor in the resultant fusion mixture. In accordance with this and similar embodiments, an antitoxin is introduced into cells of this cell population, which cell population is then fused to cells of a second population. The fusion product is then isolated by culturing the fusion mixture in the presence of an appropriate amount of the toxin.

Numerous other toxins may be utilized for the selection system depending upon the requirements of the specific cell system. For example, since rat and mouse cells are resistant to diphtheria toxin, diphtheria toxin cannot be used to eliminate non-fused parental mouse or rat cells when selecting heterokaryons or hybrids involving these cells. However, antibodies to other toxins such as ricin, abrin, modeccin, or other antitoxin antibodies should provide the flexibility necessary for using toxin-antitoxin selection for isolating rodent cell hybrids.

DETAILED DESCRIPTION OF THE PREFERRED EMBODIMENTS

Practice of the present invention to isolate cell fusion products relies on a toxin-antitoxin selection system which can be characterized as follows.

When two populations of distinct cell types are fused, by any of a number of various procedures, the initial fusion product is termed a polykaryon. A cell population, as used in the present invention, refers to any group of cells which is made up of predominantly the same cell type. The polykaryon is a bi- or multinucleate cell (i.e., two or more nuclei in the same cell) which contains the genetic and cytoplasmic complement of the two or more parental cells that have fused together. It follows, therefore, that the polykaryon has the potential to exhibit characteristics, both genetic and cytoplasmic, of the parental cells which have given rise to it.

When a fusion is performed between two populations of different cell types, three possible cell fusion products, or polykaryon types, can be expected. For example, if one fuses a hypothetical cell type A with another hypothetical cell type B, the three possible fusion products produced could be described as AA, AB, and BB, where the letters denote the parentage of the polykaryon. Of these three types of fusion products, only the AB would be a fusion of two *different* cell types, i.e., a heterokaryon. It is this heterokaryon which is important to the study of cellular gentic and control mechanisms. Therefore, the object of the present invention is to provide a method to isolate or select the heterokaryon from the homokaryons (i.e., fusion products of only one parental cell type) and non-fused parental cells.

The technique of inducing the fusion of cells is widely applicable to a large number of different cell types. Virtually every type of human, animal or plant cell may be fused both intra- and interspecifically. When cells of different organisms are fused (e.g., mouse and man; hen and rat; mosquito and man; plant and animal; plant and human), interspecific hybrids are produced. In these cases, the parental cells differ at least with respect to genotype if not phenotype as well. Intraspecific hybrids are obtained by fusing two different cell types from the same species or organism (e.g., mouse fibroblasts and mouse lymphoblasts; mouse epidermal cells and mouse lung cells; rat liver cells and rat hepatoma cells; human sarcoma cells and human liver cells). In these instances the parental cells may differ in phenotype, that is, in morphological, biochemical, immunological, or functional properties.

The toxin-antitoxin selection system relies on the observation that when the appropriate antitoxin is introduced into the cytoplasm of a cell, the antitoxin will serve as a prophylaxis against the cell killing effect of the toxin. By introducing such an antitoxin to a hypothetical toxin A, into a first cell type and an antitoxin to toxin B in a second cell type, the heterokaryon fusion product can be isolated by culturing the fusion mixture in a medium containing both toxin A and B. Therefore, the term toxin, as used in the present disclosure, refers to any molecule capable of promoting cell death for which an antitoxin is available or can be produced; the antitoxin must be capable, when introduced into the cytoplasm of the cell, of conferring resistance to or prophylaxis against the cell killing effects of the toxin.

In one embodiment of the present invention, the toxins ricin and diphtheria toxin are used to select for cell fusion products. The antitoxins which are introduced into the starting cell types in this embodiment are actually antibodies which are specific for ricin and diphtheria toxin, respectively. It has thus been determined that certain antibodies directed against the specific toxin act as antitoxins by binding to the toxin and thereby preventing the toxin from exerting a toxic effect on the cell. Therefore, antitoxin antibodies are often a good starting point for developing an antitoxin which can successfully be used in the practice of the present invention. However, any substance which will confer resistance to a cell against the toxic effects of a toxin will serve equally well in the practice of the present invention.

Likewise, numerous other toxins might be adapted to those situations where diphtheria toxin and/or ricin are incompatible with the particular fusion system being employed. For example, some rodent cells are naturally resistant to diphtheria toxin, therefore, diphtheria toxin will not be successful in isolating hybrids involving these rodent cells. In such a case, other toxins including, for example, abrin or modeccin can be utilized for isolation of rodent cell hybrids. In short, any toxin, to which an appropriate antitoxin which is capable of conferring resistance to the toxin can be made, can be used in the practice of the present invention.

The present invention is described by way of embodiments in which ricin and diphtheria toxin are utilized. These two toxins, and their respective antitoxins, are meant to be merely illustrative of one possible embodiment. Numerous other toxins may be employed in the practice of the present invention. Table I is a list of various plant, animal and microbial toxins which may be used in the practice of the present invention. However, this table should not be construed as limiting the contemplated scope of the invention.

TABLE I

Microbial Toxins

*P. aeruginosa* exotoxin
*Cl. diphtheriae* toxin (diphtheria toxin)
*S. dysenteriae* toxin
Colicin K
Colicin E2
Colicin E3
Cloacin DF13
*B. pertussis* toxin
Various endotoxins (staphylococcal, *E. coli, S. flexner,* Salmonella, other gram negative microbes)

Plant Toxins

*Ricinus communis* toxin (ricin)
*Abrus precatorius* toxin (abrin)
*Adenia digitata* (modeccin)
*Phytolacca americana* toxin
Wheat germ toxin
*Croton tiglium* toxin
*Jatropha curcas* toxin
*Momordica charantia* toxin
*Gelonium multiflorum* toxin
*Dianthus carophyllus* toxin
*Viscum album* toxin
alpha amanitin
aflatoxin
sterigmatocystin
leuteoskyrin
nivalenol
T-2 toxin
verrucarin A
roridin A
patulin
Various algal toxins (*Ulva pertusa* and *M. lyngbyaccus*)

Animal Toxins

Many families of venomous snakes produce toxic venoms quite similar to the bacterial toxins. Most crude venoms contain multiple toxic activities. Although the specific neurotoxins would probably not be useful for the present invention, some of the other activities might be applicable. The following species are exemplary:

Hydropheidae
*Enhydrina schistosa*
Elapidae
*Bungarus coeruleus* (Indian krait)
*Bungarus multicinctus*
*Dendroaspis viridis*
*Hemachatus haemachates* (Ringhals)
*Naja naja* (India cobra)

-continued

| |
|---|
| *Naja naja atra* (Formosan cobra) |
| Viperidae |
| *Bitis lachesis* (Puffotter) |
| *Echis carinatus* (saw-scaled viper) |
| *Vipera ammodytes* (sand viper) |
| *Vipera berus* (Kreuzotter) |
| *Vipera russellii* (Naboia) |
| Crotalidae |
| *Agkistrodon acutus* |
| *Bothrops atrox* (caicaca) |
| *Bothrops cotiara* (cotiara) |
| *Bothrops jararaca* (jararaca) |
| *Bothrops jararacussu* (jararacussu) |
| *Trimeresurus flavoridis* |

Starting Materials and Methods

Cells.

Although virtually any cells, may be fused using the procedures that follow, a few particular cell types have been chosen to illustrate the practice of the present invention. One of the cell types, normal human diploid embryonic lung fibroblasts (HEL 229, ATCC CCL137), was obtained from the American Type Culture Collection, Rockville, Md. The xeroderma pigmentosum cells GM2991 (complementation group A) and GM2992 (complementation group C) were obtained from the Human Genetic Mutant Cell Repository, Camden, N.J. L6 rat myoblasts were obtained from Dave Shubert at the Salk Institute. The NS-1 myeloma cells were obtained from John Porter of The University of Texas Health Science Center in Dallas.

Preparation of Antitoxin Antibodies

Antiricin monoclonal antibodies were produced by immunizing mice with formaldehyde treated ricin toxoid as follows. Due to the high toxicity of the intact toxin, the immunization of mice with ricin was performed using a toxoid prepared by formaldehyde treatment of the toxin. Ricin toxin was incubated at a concentration of 0.5 mg/ml in phosphate-buffered saline (PBS) for three days at 37° in 1% formaldehyde. This treatment leaves the antigenic determinants of the ricin toxin intact while destroying the toxic activity of the toxin. Following the three day incubation, the formaldehyde was removed by passing the mixture over a 1.0×20.0 cm Sephadex G-25 column in PBS. The excluded fractions contained the immunologically reactive toxoid which was then used for antibody production in mice.

A 0.5 mg/ml solution of the toxoid in PBS was mixed at a 1:1 ratio with complete Freund's adjuvant. 200 ul of this mixture, which contains 50 ug of the ricin toxoid, was injected into each of five mice on day 0. On days 7 and 14, the same procedure was repeated, except using incomplete Freund's adjuvant in place of the complete Freund's adjuvant. On day 35, the mice were each boosted intravenously with 20 ug of the toxoid in PBS. On day 38, the spleen from the mouse with the highest titer of antiricin antibodies was removed and used for the hybridoma fusion. After the spleen was excised, the mouse lymphocytes were expressed by squeezing the spleen using forceps. The expressed cells were centrifuged onto a ficoll/hypaque cushion (density of 1.09 g/ml). The mouse lymphocytes thus migrate to the ficoll/hypaque interface and, after harvesting, were washed in Dulbecco's modified Eagles medium, 4:1, in medium 199. The washed lymphocytes were counted and mixed with NS-1 myeloma cells at a ratio of 5:1, spleen cells to myeloma cells. This mixture was centrifuged onto two 5 cm petri dishes, the medium removed, and the dishes flooded with the above modified Eagle's medium containing 50% polyethylene glycol, molecular weight 1000, for 60 seconds. The cells were then gently rinsed twice with medium and cultured overnight in medium containing 30% fetal calf serum. The cells were then transferred to HAT medium and aliquoted into eight 96-well microtiter dishes.

Hybridoma clones were initially screened for the ability of the culture supernatent from the microtiter dish well (50 ul, diluted to a final volume of 150 ul) to prevent the lethal effects of 3 ng/ml ricin on human fibroblasts. Antibodies to both the ricin B chain (responsible for binding and uptake) and the ricin A chain (the catalytic subunit) gave positive results in this intial screening. Monoclonal antibodies with blocking activity against the catalytic ricin A chain were then identified by the ability of osmotically injected antibody (20 fold concentrated culture supernatent) to protect against the lethal effects of ricin. Positive hybridomas were then cloned and retested. One clone, designated as R6f, provided the greatest degree of protection and was used for the production of ascites fluid.

Antidiphtheria toxin polyclonal antibodies were produced by immunizing rabbits with diphtheria toxoid (Connaught Laboratories, Willowdale, Ontario, Canada). The polyclonal antibodies were concentrated fifteen fold following their precipitation in 50% ammonium sulfate, dialysis against 6 mM phosphate buffer, pH 7.2, sterile filtration and lyophilization. The antidiphtheria toxin antibodies were then dissolved in a hypertonic sucrose/PEG solution [0.5M sucrose and 10% polyethylene glycol (PEG) in serum-free medium].

Introduction of Antitoxin and Fusion of the Cells

Antibodies were injected into the cells using the technique for cells in suspension developed by Okada and Rechsteiner (*Cell*, 29:33–41, May 1982 as follows. The method below is described for use on human fibroblasts, however minor modifications (e.g., spleen cells isolated from an animal are in suspension and do not need to be trypsinized to detach them from a culture dish) would be required for different cell types. These and other modifications will be apparent to those skilled in the art.

Cultures were trypsinized, counted and centrifuged for 2 min at 700g. The supernatant was removed by first decanting the liquid, briefly recentrifuging in order to drive liquid adhering to the walls of the tubes down to the bottom, and then carefully aspirating the remaining fluid. The cell pellet was vigorously resuspended in hypertonic sucrose/PEG containing the desired antibody using 0.4 ml per $10^7$ human fibroblasts. Volumes of hypertonic antibody of less than 0.2 ml per $10^7$ fibroblasts resulted in a reduced efficiency of antibody injection. The cells were incubated in a 37° C. water bath for 10 minutes with occasional agitation to maintain the cells in suspension. The hypertonic solution (0.1–0.4 ml) was diluted by the addition of 10 ml of warm 60% serum-free medium (6:4 ratio of medium:distilled water) to hyptonically shock the cells and cause the newly formed pinosomes to burst. Two minutes later the cells were centrifuged and resuspended in isotonic medium. Two 10 ml washes (including the resuspension of the cell pellet from the hypotonic treatment) were sufficient to remove free antibody if the pellet was carefully aspirated to dryness and resuspended during each wash cycle.

The degree of protection conferred by the antibodies was assessed by comparing the survival of antibody-injected versus control cells in serial three-fold dilutions of the toxin. Cells were plated at $25-50 \times 10^3$ cells/cm$^2$ in toxin-containing medium on day 0, incubated overnight, then fed toxin-free medium, on day 1. It was not necessary to wash the cells to remove all traces of toxin, since identical results were obtained if the toxin-containing medium was simply aspirated and replaced with fresh medium. Cells treated with lethal doses of toxin generally looked reasonably healthy on day 1, sickly on day 2, and had died and detached from the dish by day 3. Experiments were generally analyzed three days after the start of the experiment. The degree of protection was calculated by dividing the LD$_{50}$ of antibody-injected cells by the LD$_{50}$ obtained using control cells.

In a typical experiment, $5 \times 10^6$ cells of each type are treated with 0.2 ml of either hypertonic antiricin ascites or antidiphtheria toxin serum, hypotonically shocked, and centrifuged. The cell pellets are resuspended in 10 ml medium and one third removed to determine the degree of toxin protection produced. These cells would later be centrifuged, washed, and plated in serial 3-fold dilutions of toxin. The remaining cells are mixed together and repelleted. The supernatent is decanted, and the tube briefly recentrifuged to remove liquid adhering to the walls. The pellet is then aspirated to dryness, and vigorously resuspended for 15 seconds in 0.2 ml of 35% v/v polyethylene glycol (MW 1000), 10% v/v dimethylsulfoxide in serum-free medium. The fusing cells are gently agitated by rolling the centrifuge tube for 45 seconds, and the reaction terminated by the addition of 10 ml of complete medium containing 10% fetal bovine serum. Newly fused cells become resistant to vigorous trituration within 15-20 minutes at room temperature. The cells are thus left at room temperature for 30 minutes, centrifuged, resuspended and plated overnight in medium containing both ricin and diphtheria toxin at the desired concentrations. Approximately 20 hours later the cells are fed toxin-free medium. The cells are fixed in 95% ethanol three days after fusion, Giemsa stained, and counted to determine the purity (% of total nuclei present in cells containing more than one nucleas) and efficiency of rescue (percent of nuclei recovered in viable heterokaryons). The best results are obtained when dividing rather than confluent cultures of human fibroblasts were used.

Approximately 80% of the cells are actually recovered following each centrifugation. Following four centrifugations the final number of cells is thus reduced to 40% of the initial value. The plating densities described refer to the actual plating densities, not those determined by initial cell counts.

EXAMPLE 1

DEGREE OF ANTITOXIN PROTECTION AFFORDED BY OSMOTIC INJECTION OF ANTIBODIES

Normal diploid human fibroblasts (HEL 229) were exposed to hypertonic solutions containing either polyclonal antidiphtheria toxin serum or monoclonal antiricin antibodies and hypotonically shocked as described in the preceding section to introduce the antibodies into the cytoplasm of the cells. The degree of protection conferred by this "osmotic injection" technique to subsequent exposure of the protected cells to diphtheria toxin and ricin was determined from the cell survival three days later following an overnight exposure to increasing toxin concentrations. In this example, the antiricin antibody provided a 140-fold increased protection against the cell killing effects of ricin. Thus, cells containing the antiricin antibodies were able to survive in a 140-fold higher concentration of ricin than cells which had not received the antiricin antibodies. Similarly, osmotic injection of antidiphtheria toxin antibodies into HEL 229 cells provided a 50-fold increase in protection against diphtheria toxin. Antiricin-injected cells exhibited no cross-protection against diphtheria toxin and vice versa.

EXAMPLE 2

PURITY AND RESCUE OF FUSED CELLS AS A FUNCTION OF TOXIN CONCENTRATION

Antiricin-injected human fibroblasts (HEL 229) were fused to antidiphtheria toxin-injected HEL 229 cells by the polyethylene glycol technique described previously, and plated at various ricin and diphtheria toxin concentrations in order to determine the purity and efficiency of cell rescue as a function of toxin concentration. At 3 ng/ml diphtheria toxin, populations in which more than 90% of the nuclei were in cells with more than one nucleus were obtained with all ricin concentrations above 1 ng/ml. The antiricin antibody confers excess protection on the cells, since the efficiency of rescue does not decline significantly with increasing ricin concentrations. In contrast, the polyclonal antidiphtheria toxin serum is providing adequate but not excess protection. Although sufficiently active to produce complete rescue of heterokaryons at concentrations that kill control cells, the efficiency of rescue declines precipitously at higher diphtheria toxin concentrations. Aliquots of control cells fixed 16 hours after cell fusion showed that 30% of the nuclei were present in cells with more than one nucleus compared to a 2-3% background in unfused cultures. If all fused cells were binucleated and half were homokaryons and half heterokaryons, then an efficiency of rescue of 14% would represent the survival of 100% of the heterokaryons. The presence of cells with more than 2 nuclei would increase the proportion of heterokaryons above 50% of the fusion products. The present data indicates that 95% pure populations can be obtained in which essentially 100% of the heterokaryons are protected against the toxins and survive.

Unambiguous proof that the cells with more than one nucleus that survived the selection procedure were in fact heterokaryons was provided by fusing antidiphtheria toxin-injected cells labeled with $^3$H-thymidine to unlabeled antiricin-injected cells. A population in which only 80% of the nuclei were in putative heterokaryons was auto-radiographed and analyzed for the distribution of labeled nuclei. In spite of the low purity of the experiment, 86% of 100 oligonucleated cells scored contained both labeled and unlabeled nuclei, and were thus authentic heterokaryons. The purity of the rescued populations as determined by the percent of nuclei in multinucleated cells therefore provides an accurate estimate of the proportion of fused cells that are true heterokaryons, even at relatively low purities.

EXAMPLE 3

TOXIN-ANTITOXIN SELECTION OF COMPLEMENTED XERODERMA PIGMENTOSUM HETEROKARYONS

Xeroderma pigmentosum is a genetic deficiency wherein cells exhibit a reduced ability to repair DNA which has been damaged by ultraviolet irradiation. The two xeroderma pigmentosum cell lines, GM 2991 (complementation group A) and GM 2992 (complementation group C), are two such cell lines. These cells are inefficient, by themselves, in repairing ultraviolet-induced damage to their DNA. However, the specific genetic defect in GM 2991 is different than in GM 2992. Therefore, when GM 2992 cells are fused to GM 2991 cells, the resultant heterokaryon fusion product shows an almost normal ability to repair such damage. The reason for this being that the genetic component of one cell type is capable of complementing the defect present in the other cell type, and vice versa. These two cell types GM 2991 and GM 2992. are therefore referred to as being from different complementation groups. The present example demonstrates the usefulness of the toxin-antitoxin selection technique in isolating complemented xeroderma pigmantosum heterokaryons, that is, heterokaryons formed from the fusion of GM 2991 and GM 2992.

This is illustrated by the experiments reflected in Table I. The control cells used, human embryonic lung cells (HEL), do not carry the xeroderma pigmentosum defect and are therefore relatively resistant to the effects of ultraviolet irradiation. Thus, the fusion product of HEL cells, designated HEL×HEL, is similarly resistant. This control cell fusion has therefore been assigned a level of DNA repair activity corresponding to 100%. When GM 2991 or GM 2992 are fused to themselves (GM 2991×GM 2991 or GM 2992×GM 2992), no complementation is possible, which is reflected in the low level of DNA repair observed both in the unselected and toxin-antitoxin-selected groups. However, when GM 2992 cells are fused with GM 2991 cells (GM 2991×GM 2992), complementation occurs and the fusion product of these two cells exhibit a near control level of DNA repair activity. The ability of the toxin-antitoxin selection process to select for the complemented heterokaryons is illustrated by the much higher level of DNA repair observed in the selected cells versus the non-selected cells. The toxin-antitoxin selection system permitted the specific behavior of the desired fusion products to be analyzed without being diluted by a presence of large numbers of non-fused parental cells.

TABLE II

COMPLEMENTATION ANALYSIS OF XERODERMA PIGMENTOSUM CELLS[1]

| Cells Fused | % DNA Repair Activity | |
|---|---|---|
| | Unselected Cells[2] | Toxin-Antitoxin Selected Cells[3] |
| HEL × HEL | 100 | 100 |
| GM 2991 × GM 2991 | 12 | 0 |
| GM 2992 × GM 2992 | 20 | 7 |
| GM 2991 × GM 2992 | 27 | 68 |

[1]Ultraviolet DNA repair was measured by determining the amount of $^3$H—Thymidine incorporation in the presence of 10 mM Hydroxyurea following 10 joules/m$^2$ irradiation at 254 nanometers.
[2]Unselected cells were fused to themselves, or mixed and then fused to each other. In the fused population, approximately 15% of the unselected cells should have been heterokaryons. Values are the mean of replicate determinations.
[3]Selected cells were isolated following an overnight treatment in 3 ng/ml diphtheria toxin and 15 ng/ml ricin. Since control experiments showed that the amount of ultraviolet-induced $^3$H—Thymidine incorporation was reduced at low cell densities, the selected cells were trypsinized and replated at confluent densitites on the second day following cell fusion, then analyzed the next day. Values are the mean of replicate determinations from two independent experiments.

EXAMPLE 4

RESCUE OF HETEROPLASMONS USING TOXIN-ANTITOXIN SELECTION

A heteroplasmon is the initial fusion product of one cell with a second, enucleated cell (i.e., a cell which contains no nucleus). A heteroplasmon will contain the nucleus and cytoplasm of one cell and in addition, the cytoplasm of the second cell. Since unfused enucleated cells or enucleated cells which have been fused to each other will not survive for long (since they lack a nucleus), there is no need to worry about them contaminating the resultant fusion products. Therefore, there is only a need for one toxin and antitoxin when selecting for heteroplasmons.

In this example, L6 rat myoblasts are enucleated by spinning cells grown in 25 cm$^2$ flasks at 20,000g for 30 minutes at 39° C. in the presence of 4 ug/ml cytochalasin B. After the cells have been allowed to recover in cytochalasin-free medium at 37° C. for 30 minutes, the anucleate cytoplats are trypsinized, pelleted and, injected with antiricin antibodies. Half of the cytoplasts are then mixed with L6 myoblasts and fused. As a control, the remaining half are fused to themselves with polyethylene glycol and then mixed with L6 myoblasts that had been fused to themselves. The cells were plated overnight in increasing concentrations of ricin, fed toxin-free medium, fixed, and Giemsa stained 4 days later. The increased survival which is observed in the experimental fusions indicates that heteroplasmons were rescued and that anucleate cytoplasts can take up sufficient amounts of antiricin antibodies to confer protection to at least a 10 fold range of otherwise lethal ricin concentrations.

EXAMPLE 5

HYBRIDOMA ISOLATION USING TOXIN-ANTITOXIN SELECTION

Hybridoma isolation has generally been accomplished using the HAT selection procedure set out above in the background section. The present example illustrates the usefulness of the toxin-antitoxin procedure in accomplishing hybridoma isolation, thus negating the need for genetically defined cells and HAT selection media.

In this example, spleen cells isolated from a non-immune mouse were osmotically injected with hypertonic antiricin antibodies as set forth above, and divided into aliquots. One aliquot was mixed with NS-1 myeloma cells, fused, then plated in HAT medium 24 hours later. The remaining cells were either fused to themselves then mixed ("mixed") or mixed with NS-1 cells and then fused ("fused"). These sets of cells were then incubated overnight in various concentrations of ricin, then plated in ricin-free medium. The results, as set forth in Table II, suggest that the toxin-antitoxin selection technique is at least an order of magnitude more effective than the HAT system for the productions of hybridoma colonies. Since a non-immunized animal was used in this example, the proportion of colonies secreting antigen-specific antibodies could not be determined.

TABLE III

HYBRIDOMA ISOLATION USING HAT AND RICIN-ANTIRICIN SELECTION

| | No. Colonies/spleen[1] | |
|---|---|---|
| | Mixed | Fused |
| HAT | — | 1,200 |
| Ricin 3 ng/ml | 3,300 | 52,200 |
| Ricin 10 ng/ml | 350 | 16,350 |

[1]The number of colonies per 96 well dish was determined 1 week after fusion. These numbers were then normalized to the results that would have been obtained fusing 250 million spleen cells to 50 million NS-1 myeloma cells.

It will be apparent to those skilled in the art that many changes in the materials, methods and amounts of materials utilized may be made without departing from the scope and spirit of the invention or compromising any of its advantages. For instance, although the examples are set forth utilizing the two specific toxins, ricin and diphtheria toxin, it is felt that any toxin to which an appropriate antitoxin can be developed, would be useful in the practice of the present invention. Examples of such toxins include, but are not limited to, abrin and modeccin. Moreover, the embodiments presented should not be construed as limiting the scope of the present invention. Those skilled in the art will recognize that the present is applicable to almost any cell fusion system and its applicability is not limited to those few cell systems presented herein by way of example.

Further modification of the invention herein disclosed will occur to persons skilled in the art who have the benefit of this disclosure, and all such modifications are deemed to be within the spirit and scope of the invention as defined by the apppended claims.

What is claimed is:

1. A method for isolating the fusion product of two cells comprising the steps:
   (a) introducing into cells of a first cell population a first antitoxin antibody that is specific for a first toxin;
   (b) introducing into cells of a second cell population a second antitoxin antibody that is specific for a second toxin, the second toxin being different from the first toxin;
   (c) mixing cells from the first antitoxin-containing first cell population with cells from the second antitoxin-containing second cell population under conditions which promote the fusion of cells of the first cell population to cells of the second cells population to produce a fusion mixture;
   (d) culturing the fusion mixture in a medium containing an amount of the first and second toxin sufficient to inhibit the survival of unfused cells and permit the survival of fused cells to thereby permit isolation of the fusion product of cells of the first cell population with cells of the second cell population; and
   (e) isolating the fusion product.

2. The method of claim 1 wherein the fusion product is a hybridoma.

3. The method of claim 1 wherein the first and second toxins are ricin and diphtheria toxins, respectively.

4. A method for isolating the fusion product of two cells comprising the steps:
   (a) introducing an antitoxin antibody that is specific for a toxin into cells of a first cell population, the first cell population being characterized by an inability to propagate in culture;
   (b) mixing cells from the antitoxin-containing first cell population with cells from a second cell population having the ability to propagate in culture, under conditions which promote the fusion of cells of the first cell population with cells of the second cell population to produce a fusion mixture;
   (c) culturing the fusion mixture in a medium containing the toxin for which the antitoxin antibody is specific, in an amount sufficient to inhibit the survival of unfused cells of the second cell population and permit the survival of fused cells to thereby isolate the fusion product of cells of the first cell population and cells of the second cell population; and
   (d) isolating the fusion product.

5. The method of claim 4 wherein the fusion product is a hybridoma.

6. The method of claim 4 wherein the toxin is selected from the group consisting of:
   (a) diphtheria toxin;
   (b) ricin;
   (c) abrin; and
   (d) modeccin.

7. The method of claim 4 wherein the first cell population is comprised of enucleated cells and the fusion product is a heteroplasmon.

8. The method of claim 1 or 4, wherein the fusion product is a polykaryon.

9. The method of claim 1 or 4, wherein the fusion product is a heterokaryon.

10. The method of claim 1 or 4, wherein the fusion product is a homokaryon.

11. The method of claim 1 or 4, wherein the fusion product is a cell hybrid.

12. The method of claim 1 or 4, wherein the fusion product is a synkaryon.

13. The method of claim 1 wherein the first toxin is selected from the group consisting of:
   (a) diphtheria toxin;
   (b) ricin;
   (c) abrin; and
   (d) modeccin; and
the second toxin is selected from the group consisting of:
   (a) diphtheria toxin;
   (b) ricin;
   (c) abrin; and
   (d) modeccin.

14. The method of claim 1 or 4, wherein the first or second toxin is an animal toxin.

15. The method of claim 1 or 4, wherein the first or second toxin is a microbial toxin.

16. The method of claim 1 or 4, wherein the first or second toxin is a plant toxin.

17. A method for isolating the fusion product of two cells comprising the steps:

(a) introducing into cells of a first cell population a first antitoxin antibody that is specific for a first toxin selected from the group consisting of ricin; abrin; modeccin; and diphtheria toxin;

(b) introducing into cells of a second cell population a second antitoxin antibody that is specific for a second toxin different from the first toxin, the second toxin selected from the group consisting of ricin; abrin; modeccin; and diphtheria toxin;

(c) mixing cells from the first antitoxin-containing first cell population with cells from the second antitoxin-containing second cell population under conditions which promote the fusion of cells of the first cell population with cells of the second cell population to produce a fusion mixture;

(d) culturing the fusion mixture in a medium containing the first and second toxin in amounts sufficient to inhibit the survival of unfused cells and permit the survival of fused cells to thereby permit isolation of a fusion product of cells of the first cell population and cells of the second cell population; and (e) isolating the fusion product.

18. A method for isolating the fusion product of two cells comprising the steps:

(a) introducing an antitoxin antibody specific for a toxin selected from the group consisting of ricin; abrin; modeccin; and diphtheria toxin, into cells of a first cell population, the first cell population being characterized by an inability to propagate in culture;

(b) mixing cells from the antitoxin-containing first cell population with cells from a second cell population having the ability to propagate in culture, under conditions which promote the fusion of cells of the first cell population with cells of the second cell population to produce a fusion mixture;

(c) culturing the fusion mixture in a medium containing an amount of the toxin for which the antitoxin antibody is specific, in an amount sufficient to inhibit the survival of unfused cells of the second cell population and permit the survival of fused cells to thereby isolate the fusion product of cells of the first cell population and cells of the second cell population; and (d) isolating the fusion product.

19. The method of claim 18 wherein the fused cell is a hybridoma.

20. The method for generating a hybrid continuous cell line which produces antibodies directed against a selected antigen comprising the steps of:

(a) immunizing a mammal with the antigen;

(b) collecting spleen cells from the immunized mammal;

(c) introducing an antitoxin antibody that is specific for a toxin selected from the group consisting of ricin; abrin; modeccin; and diphtheria toxin, into the cytoplasm of the spleen cells;

(d) mixing the spleen cells with mammalian myeloma cells under conditions which will promote the fusion of the spleen cells to the myeloma cells;

(e) culturing the fusion mixture in a medium containing an amount of the toxin for which the antitoxin antibody is specific, in an amount sufficient to inhibit the survival of unfused cells and permit the survival of the hybrid continuous cells; and (f) isolating the hybrid continuous cell line.

* * * * *

UNITED STATES PATENT AND TRADEMARK OFFICE
CERTIFICATE OF CORRECTION

PATENT NO. : 4,659,663
DATED : April 21, 1987
INVENTOR(S) : Woodring E. Wright

It is certified that error appears in the above-identified patent and that said Letters Patent is hereby corrected as shown below:

Column 1, line 6, delete "THe" and insert
--The--.

Column 2, line 12, delete "hetefokaryons" and insert
--heterokaryons--.

Column 5, line 17, delete "gentic" and insert
--genetic--.

Column 6, line 31, delete "Cloacin" and insert
--Colicin--.

Column 13, line 60, delete "second cells" and insert
--second cell--.

Signed and Sealed this

Twenty-second Day of September, 1987

Attest:

DONALD J. QUIGG

Attesting Officer     Commissioner of Patents and Trademarks